(12) United States Patent
Macours

(10) Patent No.: US 8,477,984 B2
(45) Date of Patent: Jul. 2, 2013

(54) ELECTRONIC CIRCUIT FOR HEADSET

(75) Inventor: Christopher Marc Macours, Hodeige (BE)

(73) Assignee: NXP B.V., Eindhoven (NL)

( * ) Notice: Subject to any disclaimer, the term of this patent is extended or adjusted under 35 U.S.C. 154(b) by 521 days.

(21) Appl. No.: 12/858,880

(22) Filed: Aug. 18, 2010

(65) Prior Publication Data

US 2011/0051947 A1    Mar. 3, 2011

(30) Foreign Application Priority Data

Aug. 28, 2009    (EP) ...................................... 09168981

(51) Int. Cl.
*H04R 25/00*    (2006.01)

(52) U.S. Cl.
USPC ............................................. 381/380; 381/74

(58) Field of Classification Search
USPC ............... 381/71.1–71.4, 94.1–94.4, 74, 312, 381/316, 317, 322, 328, 380, 381; 600/25, 600/486; 607/55–57
See application file for complete search history.

(56) References Cited

U.S. PATENT DOCUMENTS

| | | | | |
|---|---|---|---|---|
| 6,004,274 A | * | 12/1999 | Nolan et al. | 600/486 |
| 2006/0140425 A1 | * | 6/2006 | Berg et al. | 381/312 |
| 2008/0205679 A1 | * | 8/2008 | Darbut et al. | 381/328 |
| 2008/0219486 A1 | * | 9/2008 | Goldstein et al. | 381/312 |
| 2009/0010461 A1 | * | 1/2009 | Klinghult et al. | 381/309 |

FOREIGN PATENT DOCUMENTS

| | | |
|---|---|---|
| JP | 2002-135887 A | 5/2002 |
| WO | 2005/029911 A1 | 3/2005 |

OTHER PUBLICATIONS

Extended European Search Report for European Patent Appln. No. 09168981.0 (Mar. 5, 2010).

* cited by examiner

*Primary Examiner* — Lun-See Lao

(57) ABSTRACT

An electronic circuit (100) is disclosed for processing signals ($20_L$, $20_R$) originating from respective signal recorders (20) integrated in respective earpieces of a headset. The electronic circuit comprises a first input for receiving a signal ($20_L$) from the signal recorder of the ear piece intended for a left ear of a wearer of the headset, said signal relating to a blood pressure pulse (200) of said wearer; a second input for receiving a further signal ($20_R$) relating to said blood pressure pulse from the signal recorder of the ear piece intended for a right ear of the wearer; a detection unit (110, 120) for detecting the order in the signal and the further signal are recorded by said respective signal recorders and for comparing the detected order with a correct order; and a signal adaptation unit (130) for adapting an output signal ($30_L$, $30_R$) in response to the detection unit signaling a detection of an incorrect order of the signal and the further signal. A method for detecting the placement of an earpiece of a headset in the intended ear (10) of the wearer of the headset is also disclosed.

15 Claims, 3 Drawing Sheets

ELECTRONIC CIRCUIT FOR HEADSET

Figure 1:
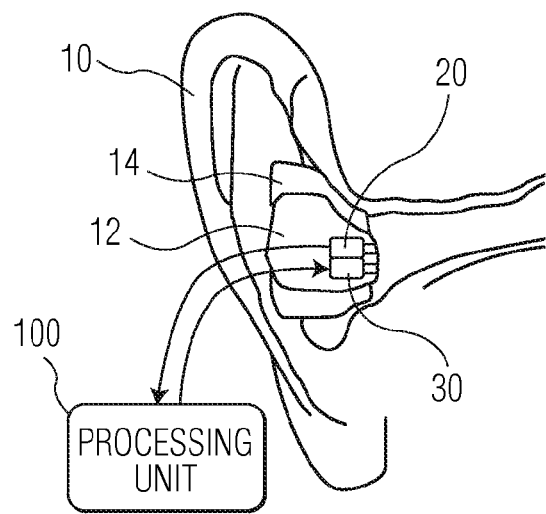

This application claims the priority under 35 U.S.C. §119 of European patent application no. 09168981.0, filed on Aug. 28, 2010, the contents of which are incorporated by reference herein.

FIELD OF THE INVENTION

The present invention relates to an electronic circuit for processing audio signals from microphones integrated in the respective earpieces of a headset.

BACKGROUND OF THE INVENTION

Headset or headphone listening is becoming increasingly popular, for instance because of to the increasing penetration of portable audio players such as MP3 players into the consumer market. Even mobile phones nowadays allow audio playback, e.g. music playback, on stereo headphones.

Another noticeable trend is the growing use of Active Noise Reduction (ANR) headphones, which attempt to isolate the user from the ambient sounds such as car or aircraft engine noise, fan noise, traffic noise and so on, by means of anti-sound played through the headphone loudspeakers. The anti-sound is calculated from microphones placed on (so-called feed-forward ANR) or inside (so-called feed-back ANR) the headphone.

The feed-back ANR configuration is particularly interesting as the microphone is not only capable of capturing external noise that penetrates the earpiece as well as the audio signals that are being played back by the earpiece loudspeakers, but is also capable of recording sounds that emanate from the user's body, such as breathing and heart rhythm. This works especially well when the earpiece is tightly fitted into the ear.

A usual problem encountered while using any type of stereo headset is the need to respect the left/right order, i.e. ensuring that the correct earpiece is placed in or on the correct ear. A left/right inversion is not dramatic in case of music listening, but in case of movie playback and augmented reality systems such as auditory displays, a left/right inversion has a negative impact on the overall experience because in these situations, a correlation exists between the sounds played over the earpieces and the physical location of the user or the directionality of events such as moving images on a movie screen to which the sounds relate.

Although most headsets are marked with a "L" on the left earpiece and a "R" on the right earpiece, the user may choose to ignore these indications, which can lead to the earpieces being placed in or on the incorrect ear. Some other conventions exist to help the user place the correct earpiece in or on the correct ear, such as asymmetric design features, e.g. a cable plug on the left side only for full-size headphones or a shorter cable portion on the left side for in-ear headphones. However, these measures do not prevent the user from ignoring these design features.

SUMMARY OF THE INVENTION

The present invention seeks to provide an electronic circuit that detects the inversion of the left/right order of a headset by a user.

According to an aspect of the present invention, there is provided an electronic circuit for processing signals originating from respective signal recorders, each of said signal recorders being integrated in a respective earpiece of a headset, comprising a first input for receiving a signal from the signal recorder of the ear piece intended for a left ear of a wearer of the headset, said signal relating to a blood pressure pulse of said wearer; a second input for receiving a further signal relating to said blood pressure pulse from the signal recorder of the ear piece intended for a right ear of the wearer; a detection unit for detecting the order in the signal and the further signal are recorded by said respective signal recorders and for comparing the detected order with a correct order; and a signal adaptation unit for adapting an output signal in response to the detection unit signaling a detection of an incorrect order of the signal and the further signal.

The present invention is based on the realization that the delay in the occurrence of the same blood pressure pulse in the right ear and left ear, as disclosed in U.S. Pat. No. 6,004,274, can be utilized to detect the correct left/right order of headset earpieces worn by a user. To this end, the electronic circuitry may generate a warning signal upon detection of the earpiece inversion, which may be an optical signal or an audible signal provided to at least one of the earpiece loudspeakers of the headset.

In a preferred embodiment, the signal adaptation circuit is adapted to interchange the audio signals for the respective earpieces in response to the detection circuit signaling an incorrect order of the signal and the further signal. Consequently, the left/right order is dynamically adapted, which has the advantage that the user does not have to interchange the earpieces upon detection of the incorrect left/right order. In other words, the correct left/right order of the provided audio signals is always guaranteed regardless of the placement of the earpieces in or on the correct ear.

The electronic circuit may be integrated in a headset comprising a pair of earpieces, wherein each earpiece comprising a signal recorder for recording the occurrence of a blood pressure pulse occurring in the ear of the wearer of the headset to which the earpiece is fitted. The respective signal recorders may be blood pressure sensors. Preferably, the respective signal recorders are microphones, such as the microphones of an active noise reduction headset.

Alternatively, the electronic circuit may be integrated in an adaptor for connecting a headset to an audio apparatus, or in an apparatus for providing audio signals to a headset, such as an audio player, a mobile phone, a multimedia player, which may be integrated into a vehicle such as a car, train or airplane, and so on.

According to another aspect of the present invention, there is provided a method of detecting the placement of an earpiece of a headset in the intended ear of the wearer of the headset, comprising receiving a signal from a signal recorder of the ear piece intended for a left ear of a wearer of the headset, said signal relating to a blood pressure pulse of said wearer; receiving a further signal relating to said blood pressure pulse from a signal recorder of the ear piece intended for a right ear of the wearer; detecting the order in the signal and the further signal are recorded by said respective signal recorders; comparing the detected order with a correct order; and adapting an output signal in response to the detection of an incorrect order of the signal and the further signal.

This method facilitates the detection of the incorrect left/right order of a bi-aural, e.g. stereo, headset when worn by a user of the headset.

Preferably, said adapting step comprises interchanging the signals for the respective earpieces in response to the detection of an incorrect order of the signal and the further signal. This has the advantage that the correct left/right order is restored without requiring user intervention, i.e. interchanging the earpieces of the headset.

BRIEF DESCRIPTION OF THE EMBODIMENTS

Figure 2:
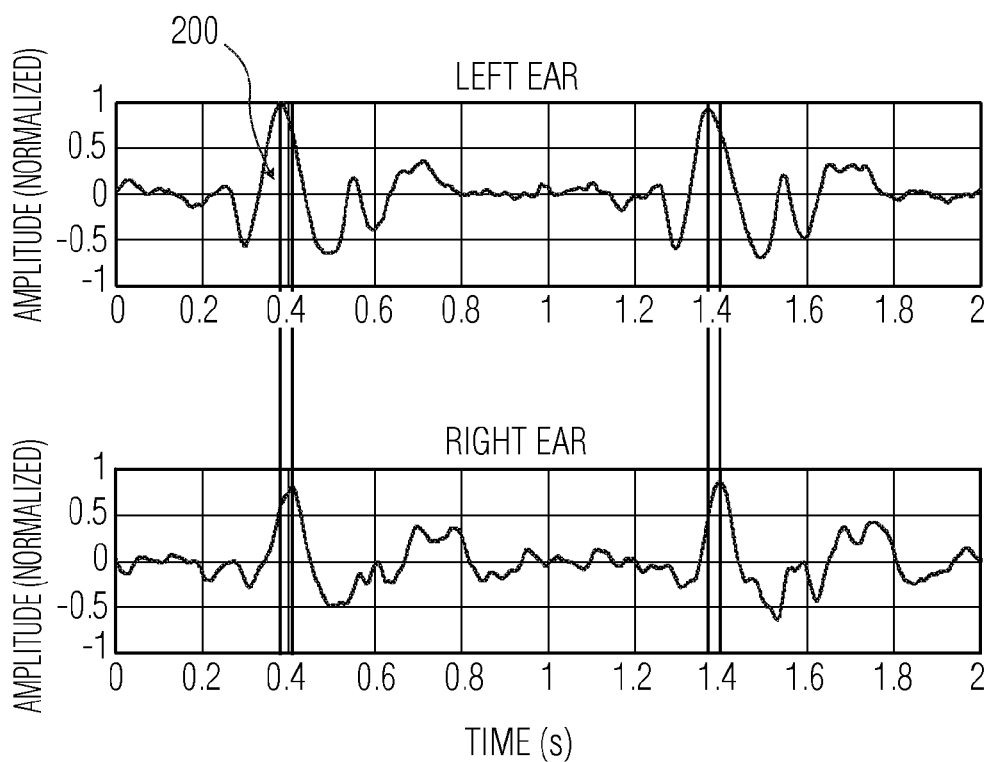
Figure 3:
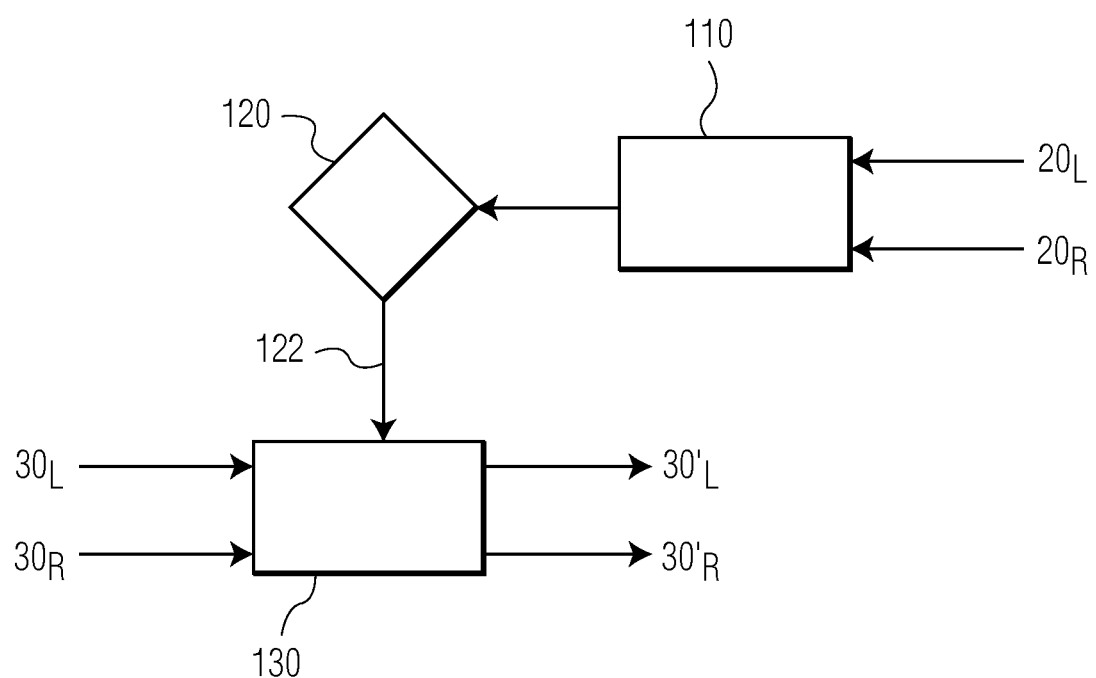
Figure 4:
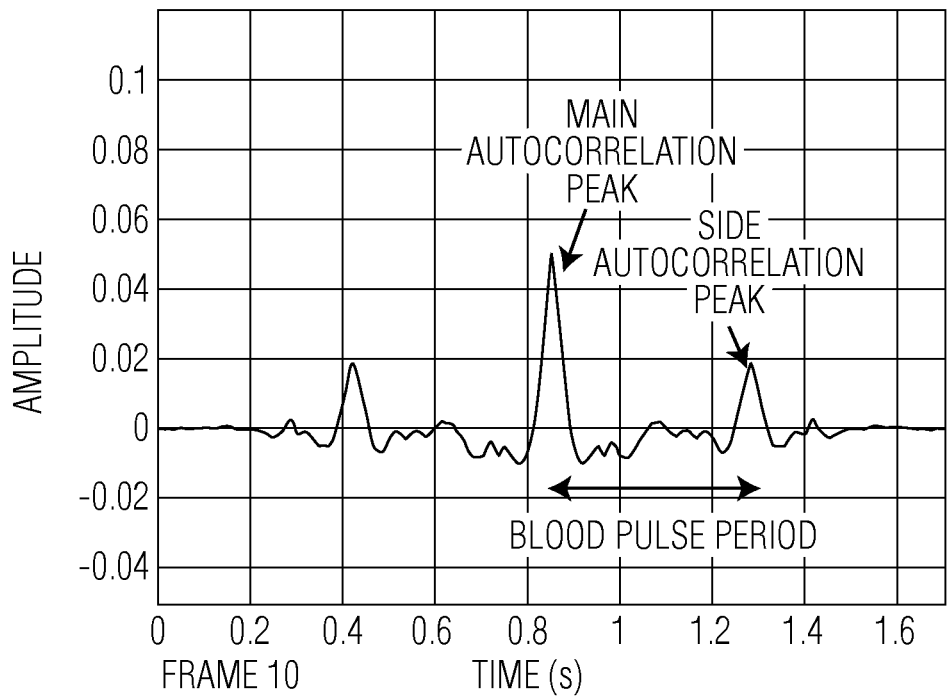
Figure 5:
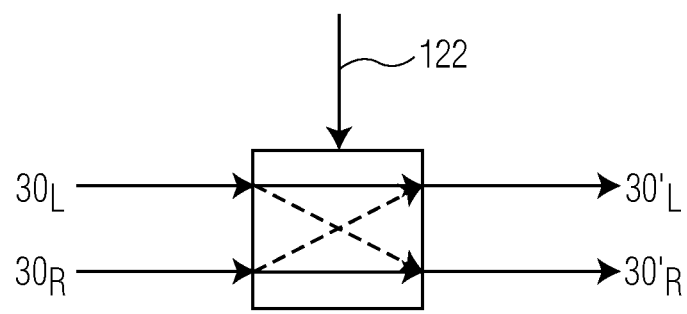

Embodiments of the invention are described in more detail and by way of non-limiting examples with reference to the accompanying drawings, wherein FIG. 1 schematically depicts an aspect of the present invention;

FIG. 2 schematically depicts blood pressure data recorded from the left and right ear of a human;

FIG. 3 schematically depicts an electronic circuit in accordance with an embodiment of the present invention;

FIG. 4 schematically depicts the autocorrelation function of a recorded low-pass filtered blood pressure signal retrieved from a human ear; and FIG. 5 schematically depicts an aspect of a preferred embodiment of the electronic circuit of the present invention.

DETAILED DESCRIPTION OF THE DRAWINGS

It should be understood that the Figures are merely schematic and are not drawn to scale. It should also be understood that the same reference numerals are used throughout the Figures to indicate the same or similar parts.

FIG. 1 demonstrates the principle of the present invention. The earpieces 12 of a headset (not shown) each have a loudspeaker 30 and a blood pressure pulse detector 20, and each earpiece 12 preferably is placed in (but may also be placed over) the cavity of an ear 10 of a wearer of the headset (the right ear is shown in FIG. 1). The earpiece 12 typically comprises some sealing or cushioning 14 to comfortably fit the earpiece in or on the ear 10. An electronic circuit 100 is adapted to receive the recorded data from both blood pressure pulse detectors 20 and to provide the loudspeakers 30 (when present) with an audio signal. The blood pressure pulse detector 20 may be a microphone although other embodiments such as a blood pressure sensor may also be used. In case of the blood pressure pulse detector 20 being implemented by a device other than a microphone, this device may be additional to a microphone in the earpiece 12 of the headset. However, if the presence of a microphone is required, e.g. because the headset is an ANR headset, it is preferred that the blood pressure pulse detector 20 is the same microphone as the microphone used for the noise cancellation because this is the most cost-effective implementation of the present invention.

The electronic circuit 100 is designed to verify if the wearer of the headset has obeyed the correct left/right order, i.e. is wearing the earpieces intended for the right and left ear in or on the correct ears. The electronic circuit 100 exploits the principle disclosed in U.S. Pat. No. 6,004,274. FIG. 2, which depicts the recording of blood pressure data including blood pressure pulses, i.e. systolic maxima, 200 as recorded by the respective microphones in the left ear (top graph) and right ear (bottom graph) of the wearer of an ANR headset.

As is clearly demonstrated in FIG. 2, the systolic maximum 200 in the blood pressure for the same heartbeat appears in the left ear before it appears in the right ear. This is because the path length of the blood to reach the right ear through the carotid artery is longer than the path length of the blood to reach the left ear through this artery. This phenomenon may be exploited by measuring the order in which these respective systolic maxima are recorded. The blood pressure pulse detector 20 in the left ear should detect the occurrence of the systolic maximum 200 before the blood pressure detector 20 in the right ear. If the opposite order is detected, i.e. the blood pressure detector 20 intended for the right ear is first to detect the systolic maximum 200, the electronic circuit 100 has detected a violation of the intended left/right order, i.e. the wearer is wearing the headphones the wrong way around.

FIG. 3 shows an embodiment of an electronic circuit 100 of the present invention in more detail. The electronic circuit 100 comprises a blood pulse order detection unit 110, which has a first input for receiving a signal 20L from the blood pressure pulse recorder 20 in the earpiece intended for the left ear and a second input for receiving a signal 20R from the blood pressure pulse recorder 20 in the earpiece intended for the right ear. The blood pulse order detection unit 110 is arranged to detect the respective points in time in which the systolic maxima 200 appear in the respective signals 20L and 20R. The detection unit 110 may use any suitable noise cancellation technique to detect the systolic maxima in the raw data signals 20L and 20R. Alternatively, any suitable signal cross-correlation technique may be used.

For instance, a low-pass filter (not shown) may be applied to filter out frequencies exceeding 20 Hz from the raw signal data, after which an auto-correlation technique may be applied on the filtered signals from the microphones in the left and right ear to determine the periodicity of these signals. For instance, as is shown in FIG. 4, which depicts a filtered signal collected from an ear of a wearer of the headset of the present invention, the difference between the main autocorrelation signal and one of its side bands can be used to determine the periodicity and duration of the blood pulse. Such side bands typically clearly appear in the signal if the signal is free from interference, e.g. body noise, voice etcetera. The time-dependent occurrence of the respective (side) bands in the filtered signals may be used to determine the delay between these bands in the respective signals, i.e. the signals captured from the left and right ear. Since such techniques are known per se, they will not be further explained for reasons of brevity only.

A delay comparison unit 120, which may be integrated in the detection unit 110, is arranged to determine the sign of the delay between the occurrence of a systolic maximum 200 in data signal 20L and the corresponding systolic maximum 200 in data signal 20R and compare this sign with the correct sign corresponding to the systolic maximum 200 in the data signal $20_L$ appearing before the systolic maximum 200 in data signal $20_R$. In case the correct occurrence order of the systolic maxima 200 has been observed, the electronic circuit 100 will not have to take any further action. However, upon detection of the incorrect order, the delay comparison unit 120 may generate an error signal 122 and provide the signal adaptation unit 130 with this error signal.

The signal adaptation unit 130 may generate a warning signal for the wearer of the headset to let the wearer know that the left/right order of the ear pieces has been violated. This may for instance be achieved by generating a visible signal, e.g. a flashing LED or a message on a display of an electronic device connected to which the headset is connected. More preferably, the signal adaptation unit 130 is arranged to receive the respective signals 30L and 30R for the loudspeakers in the left ear and right ear of the wearer, with the signal adaptation unit 130 being adapted to add the warning signal to at least one of these signals such that at least one of the output signals $30'_L$, $30'_R$ for the loudspeakers in the respective ears of the wearer of the headset generated by the signal adaptation unit 130 is adapted compared to its input signal equivalent. The inclusion of a warning signal or a warning message in the output signals 30' L and/or 30' R encourages the wearer of the headset to take corrective action, i.e. swap the earpieces. This may for instance be undesirable when the wearer is controlling a vehicle in motion, when the warning signal or message may distract the headset wearer, and also because the headset wearer is incapable of swapping the earpieces of the headset around in such situations.

In the embodiment of the signal adaptation unit 130 as shown in FIG. 5, such user intervention is avoided altogether. As shown in FIG. 5, each input $30_L$, $30_R$ has two selectable signal paths through the signal adaptation unit 130; the signal paths indicated by the solid arrows, which connect $30_L$ to $30'_L$ and $30_R$ to $30'_R$, and the signal paths indicated by the dashed arrows, which connect $30_L$ to $30'_R$ and $30_R$ to $30'_L$.

The adaptation unit 130 is adapted to select the paths indicated by the solid arrows when the systolic maxima 200 have been detected in the correct order, which is indicative of the observance of the correct left/right order by the wearer of the headset, as previously explained. However, upon detection of the incorrect order of the systolic maxima by the delay comparison unit 120, the error signal 122 generated by the delay comparison unit 120 triggers the signal adaptation unit 130 to select the signal paths as indicated by the dashed arrows such that the correct left/right order of the signals $30_L$, $30_R$ is restored. In other words, in this embodiment, the user of the headphones may wear the earpieces in any order because the signal adaptation unit 130 will ensure that the signals intended for the left and right ears will be provided to these ears by selection of the appropriate signal paths.

The electronic circuit 100 may be integrated in a headphone. Alternatively, the electronic circuit 100 may be provided as a separate adaptor such that the electronic circuit 100 may be used with pre-existing headphones and electronic equipment. In a further embodiment, the electronic circuit 100 may be integrated in an electronic device such as a media player, as long as the electronic device is configured to receive the data from the blood pressure pulse recorders 20.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. An electronic circuit for processing signals originating from respective signal recorders, each of said signal recorders being integrated in a respective earpiece of a headset, comprising:
   a first input for receiving a first signal from the signal recorder of the ear piece intended for a left ear of a wearer of the headset, said first signal relating to a blood pressure pulse of said wearer;
   a second input for receiving a second signal relating to said blood pressure pulse from the signal recorder of the ear piece intended for a right ear of the wearer;
   a detection unit for detecting the order in the first signal and the second signal are recorded by said respective signal recorders and for comparing the detected order with a correct order; and
   a signal adaptation unit for adapting an output signal in response to the detection unit signaling a detection of an incorrect order of the first signal and the second signal.

2. The electronic circuit of claim 1, wherein the adapted signal is a signal for the headset.

3. The electronic circuit of claim 1, wherein the first signal and the second signal originate from respective blood pressure sensors in the headset.

4. The electronic circuit of claim 1, wherein the first signal and the second signal originate from respective microphones in the headset.

5. The electronic circuit of claim 1, wherein the signal adaptation circuit is adapted to generate a warning signal and provide at least one of said earpieces with the warning signal in response to the detection circuit signaling an incorrect order of the first signal and the second signal.

6. The electronic circuit of claim 1, wherein the signal adaptation circuit is adapted to interchange the signals for the respective earpieces in response to the detection circuit signaling an incorrect order of the first signal and the second signal.

7. A headset comprising a pair of earpieces, each earpiece comprising a signal recorder for recording an occurrence of a blood pressure pulse occurring in an ear of the wearer of the headset to which the earpiece is fitted, the headset further comprising the electronic circuit of claim 1.

8. The headset of claim 7, wherein the respective signal recorders are blood pressure sensors.

9. The headset of claim 7, wherein the respective signal recorders are microphones.

10. The headset of claim 7, wherein each earpiece further comprises a loudspeaker.

11. The headset of claim 7, wherein the headset is an active noise reduction headset.

12. An adaptor for connecting a headset to an audio apparatus, the adaptor comprising the electronic circuit of claim 1.

13. An apparatus for providing audio signals to a headset, the apparatus comprising the electronic circuit of claim 1.

14. A method of detecting the placement of an earpiece of a headset in an intended ear of a wearer of the headset, comprising:
   receiving a first signal from a signal recorder of the ear piece intended for a left ear of the wearer of the headset, said first signal relating to a blood pressure pulse of said wearer;
   receiving a second signal relating to said blood pressure pulse from a signal recorder of an ear piece intended for a right ear of the wearer;
   detecting an order in which the first signal and the second signal are recorded by said respective signal recorders;
   comparing the detected order with a correct order; and
   adapting an output signal in response to the detection of an incorrect order of the first signal and the second signal.

15. The method of claim 14, wherein said adapting step comprises interchanging the signals for the respective earpieces in response to the detection of an incorrect order of the first signal and the second signal.

* * * * *